United States Patent [19]

Oppici

[11] 3,953,513

[45] Apr. 27, 1976

[54] PROCESS FOR PREPARING α-AMINOALCOHOLS

[75] Inventor: Ernesto Oppici, Milan, Italy

[73] Assignee: Gruppo Lepetit S.p.A., Milan, Italy

[22] Filed: Nov. 8, 1974

[21] Appl. No.: 521,997

[30] Foreign Application Priority Data
  Nov. 29, 1973 United Kingdom............ 55347/73

[52] U.S. Cl............................................. 260/585 C
[51] Int. Cl.$^2$......................................... C07C 89/02
[58] Field of Search................... 260/585 C, 584 C

[56] References Cited
UNITED STATES PATENTS

| | | | |
|---|---|---|---|
| 2,477,943 | 8/1949 | Robinson, Jr. ................ | 260/585 C |
| 3,448,153 | 6/1969 | Cavitt et al. ................ | 260/585 C X |
| 3,824,269 | 7/1974 | Tomalia et al. ............ | 260/584 C X |
| 3,879,464 | 4/1975 | Kalopissis.................. | 260/584 C |

*Primary Examiner*—Allen B. Curtis
*Attorney, Agent, or Firm*—Theodore Post; C. Kenneth Bjorh

[57] ABSTRACT

Process for preparing an α-aminoalcohol of formula

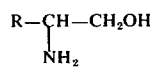

wherein R represents hydrogen or alkyl of from 1 to 5 carbon atoms, which comprises contacting a compound of formula

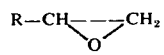

wherein R has the same meaning as above, with an alcohol of formula R'-OH wherein R' represents benzyl or the group

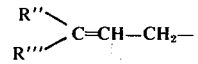

in which R" and R''' are independently selected from hydrogen and alkyl of from 1 to 4 carbon atoms in an organic solvent, in the presence of a basic catalyst, at from about 140° to about 170°C., treating the obtained product of formula

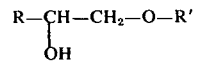

wherein R and R' have the above meanings, with at least an equimolecular amount of a p-toluene-sulfonyl halide, at from about −5° to about 20°C. in the presence of a tertiary organic nitrogen-containing base and reacting in a closed system the resulting compound of formula

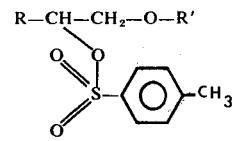

wherein R and R' are as above defined, with an excess of gaseous ammonia, in the presence of an inert organic solvent, at from about 95° to about 120°C. and recovering the resulting product as its acid addition salt.

6 Claims, No Drawings

PROCESS FOR PREPARING α-AMINOALCOHOLS

The present invention is concerned with a new process for preparing α-aminoalcohols of the general formula I

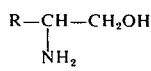

wherein R represents hydrogen or a straight or branched alkyl chain containing from 1 to 5 carbon atoms, and the acid addition salts thereof. Examples of these salts are the hydrochloride, hydrobromide, hydroiodide, sulfate, phosphate, methanesulfonate, cyclohexylsulfonate, p-toluenesulfonate and the like. From these salts the corresponding free bases may be obtained, by treating the selected salt with an equimolecular amount of a suitable basic agent, such as, for instance, an alkali hydroxide. Most of the methods employed until now for the synthesis of α-aminoalcohol derivatives substantially consist in the catalytic reduction of the corresponding α-nitroalcohols. Though the yields of the reductive step are generally quite good, the preparation of the starting α-nitroalcohols is quite tedious and difficult, especially with respect to the synthesis of the lower terms of this series, which are very heat-sensitive liquids and cannot advantageously be recovered by distillation from the reaction medium in which they are prepared by reacting a suitable 1-nitroalkane with formaldehyde under chemical conditions similar to those of an aldol-condensation (see for instance East German Patent 58516 and J. D. Roberts and M. C. Caserio, Basic Principles of Organic Chemistry, page 680, W. A. Benjamin Inc., New York-Amsterdam 1965). Moreover, it is also known that suitable methods for introducing the —NO₂ group exclusively onto the desired position of an alkyl chain do not exist in a general sense: as a matter of fact the nitration of an alkane is a non specific reaction with a radical mechanism, which gives as the final products complex mixtures of mono- and poly-substituted derivatives, even with a number of carbon atoms lower than that of the starting alkane, which can be isolated by fractional distillation only with great difficulty.

It is therefore clear that the old procedures for preparing α-aminoalcohols present several drawbacks which make them antieconomic chiefly in view of the waste of useful starting and intermediate materials and the necessity of operating under strictly controlled conditions: in other words, in view of the low overall yields.

On the other hand, a convenient process for preparing α-aminoalcohols is quite desirable, especially if one considers that the compound of formula I above wherein R is ethyl is the key-intermediate for preparing the well known antitubercular substance (+)-N,N'-bis-(1-hydroxy-2-butyl)-1,2-diaminoethane (ethambutol).

It is therefore the main object of the present invention to provide a new, simple and useful method for preparing the above α-aminoalcohols of formula I.

Accordingly, in the process of the invention, inexpensive commercially available products are used as the starting materials and we have also found that the conversion of one intermediate into a second intermediate according to the scheme which will be outlined below takes place so smoothly that the final compounds of the above formula I are obtained with yields generally higher than 75%.

The process may be represented by the following three-steps scheme:

1) 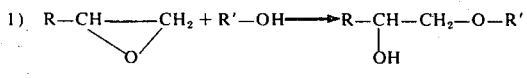

2) 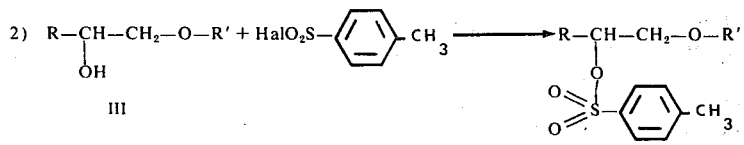

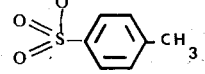

3) 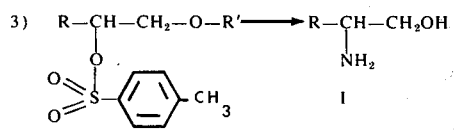

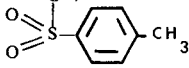

wherein R has the meaning given above, R' represents benzyl or a group

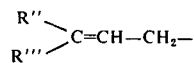

in which R'' and R''' are independently selected from hydrogen and alkyl containing from 1 to 4 carbon atoms, and Hal represents a halogen atom of the group chlorine or bromine.

Whereas the process may occur with a wide variety of 1,2-alkylene oxides of the formula

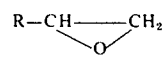

and alcohols of the formula R'-OH, it has been found that excellent results are obtained when 1,2-epoxybutane and benzyl alcohol are used as the reactants. Thus, according to step (1) of the above schema a compound of formula I is reacted with an alcohol R'OH in the presence of an organic solvent which may be selected, for example, from benzene, ethyl acetate, diethyl ether, tetrahydrofuran and the like; an excess of the alcohol itself can advantageously be employed as solvent. Usually an excess of from about 5 to about 7 molar equivalents of the alcohol is employed.

A catalytic amount of a basic catalyst, e.g. an alkali metal is required to speed up the condensation step, which may occur at very wide ranges of temperature, the most preferred one being between about 140° and about 170°C.

The reaction is generally completed within 2–4 hours, then the obtained compound of formula III is contacted with a slight excess of a halide of the p-toluenesulfonic acid, generally p-toluenesulfonyl chloride, according to step (2) of the above outlined scheme. The presence of a base is needed in this case, to block the halogenic acid which forms in the course of the reaction. Suitable basic agents for this purpose are the tertiary organic nitrogen containing bases, as for instance the tri-alkylamines in which the alkyl group consists of from 1 to 4 carbon atoms. However, pyridine or its methyl derivatives are preferably employed since they act both as the acid blocking agents and as the solvent.

The sulfonylation reaction is carried out at temperatures usually ranging from about −5° and about 20°C and is completed within about 24 hours. Compound IV forms, which is treated in a closed system according to step (3) of the proposed scheme with a large molar excess of gaseous ammonia (e.g. from about 40 to about 60 molar excess or more) under pressure at a temperature varying from about 95° to about 120°C, in the presence of an inert organic solvent which is advantageously selected from aliphatic alkanols of from 1 to 4 carbon atoms, tetrahydrofuran, dioxane and the like. During this step the ammonia pressure initially increases and then decreases somewhat after the ammonia uptake has ceased. After cooling, the reaction mixture is mixed with an amount of an alkali metal hydroxide, then several extractions with benzene and subsequently with a large amount of a cold aqueous solution of hydrochloric acid are carried out. The acidic portion is refluxed for about 2–4 hours until an oil separates essentially consisting of a substance of formula R'-Hal, wherein R' and Hal have the above meanings, which is removed from the reaction medium by vapor-phase distillation. The residue is worked up following procedures which are entirely familiar to a skilled chemist, thus obtaining the compound of the formula I in the form of its hydrochloride. If desired the free base may be prepared according to conventional methods, by treating for instance said hydrochloride with an equimolecular amount of a base, for example an alkali metal hydroxide.

It results from the above outlined reaction scheme that the compounds of the general formula I or their acid addition salts are generally obtained as a mixture of the two possible optically active isomers, owing to the presence of the asymmetric carbon atom bearing the amino group.

It is therefore intended that the separation of the two isomers into the pure optically active forms falls within the scope of the invention. This resolution is achieved according to known procedures, such as for instance through the formation of salts having different solubilities with optically active acids. Suitable acids are the mandelic, the malic, the camphorsulfonic, the glutamic or the like. The resulting salts may be separated by fractional crystallization and the free pure optically active isomers recovered from the corresponding salt by reaction with a suitable amount of an alkali agent.

The following example describes in detail one preferred embodiment of the process of the present invention.

EXAMPLE

Preparation of 2-amino-1-butanol

A. 1-Benzyloxy-2-butanol 15.4 Grams (0.67 mole) of sodium are poured into a flask containing 3.500 g. (35.2 mole) of benzyl alcohol under nitrogen atmosphere. After the sodium is dissolved, the temperature is brought to 160°C, then 481 g. (6.7 mole) of 1,2-epoxybutane are added dropwise. The temperature is kept at 160°C during the approximately 2 hours addition period. The temperature is subsequently lowered to 120°C and the excess of the starting 1,2-epoxybutane is distilled off; then 33.8 g (0.335 mole) of concentrated sulfuric acid and 36 ml. of water are added to the reaction mixture and the resulting solid sodium sulfate is removed by filtration. The filtrate is distilled under reduced pressure, thus recovering pure 1-benzyloxy-2-butanol in a yield of 90%. B.p. 128–132/6 mmHg.

B. 1-Benzyloxy-2-butanol-p-toluenesulfonate

To a solution of 1,000 g. (5.45 mole) of 1-benzyloxy-2-butanol in 2,000 ml. of pyridine, 1,170 g. (6.04 mole) of p-toluenesulfonyl chloride is added in small portions for a period of about 30 minutes at room temperature. During the addition the temperature raises, but it is kept at the room values by cooling the reaction mixture by an external circulation of ice-water; then the solution is vigorously stirred always at room temperature for about 16–20 hours. After cooling to 0°C, the solution is poured into ice-water and an oil precipitates, which is separated from the aqueous phase by decantation. The remaining water portion is twice extracted with benzene; then the oily and the benzene phases are combined together and the resulting benzene solution is cooled to about 10°C. Said organic solution is subsequently washed with concentrated hydrochloric acid, then with a saturated solution of sodium bicarbonate and finally with water, and dried over sodium sulfate. After distillation of the solvent a residue is obtained which is 1-benzyloxy-2-butanol p-toluenesulfonate which decomposes upon distillation. Yield of this step: 100%.

C. 2-Amino-1-butanol 2,700 Milliliters of ethanol and 900 g. (2.7 mole) of 1-benzyloxy-2-butanol p-toluenesulfonate are poured into an autoclave, then 800 g. (47 mole) of gaseous ammonia are added until a pressure of about 5 atmospheres is reached. The temperature is allowed to raise to about 100°–110°C, while the reaction mixture is kept under stirring and an ammonia pressure of 25–26 atmospheres is reached, which decreases to 22–23 after the ammonia uptake has ceased. The reaction mixture is allowed to cool, the unreacted ammonia is eliminated, and the obtained residue is poured into a flask, concentrated under vacuum and dissolved with a solution of 116 g. (2.9 mole) of sodium hydroxide in 665 ml. of water. The aqueous alkaline solution is repeatedly extracted with benzene, the organic phase is washed with water and then extracted three times with 600 ml. of a cold 25% aqueous solution of hydrochloric acid. The acidic extracts are combined together and the obtained mixture is refluxed for 2- 3 hours. During this stage an oil separates, consisting of benzyl chloride, which is removed from the reaction medium by vapor-phase distillation. The remaining aqueous phase is then concentrated under vacuum to small volume, the obtained oily residue is extracted with benzene, and the benzene solution is cooled to about 5°C until a solid crystalline precipitate forms, which is recovered by filtration and dried over phosphorus pentoxide. Yield of this step: 77%.

The obtained compound is the hydrochloride of 2-amino-1-butanol (M.p. 78°-80°C).

To obtain the free 2-amino-1-butanol, 46.2 g. (1.122 mole) of sodium hydroxide are added to 1.103 ml. of absolute ethanol and the resulting mixture is refluxed until the sodium hydroxide is dissolved. To this warm solution 144.5 g. (1.122 mole) of 2-amino-1-butanol hydrochloride are added under stirring for about 30 minutes and again cooled to about −10°C.

The formed sodium chloride is eliminated by filtration, and the filtrate is concentrated to small volume under vacuum. The residue is distilled under reduced pressure, thus obtaining 2-amino-1-butanol with a yield of 98.5%. B.p. 178°C.

I claim:

1. A process for preparing an α-aminoalcohol of formula

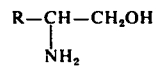    I wherein R represents hydrogen or alkyl of from 1 to 5 carbon atoms which comprises contacting a compound of formula

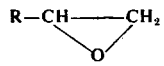    II wherein R has the same meaning as above, with an alcohol of formula R'-OH wherein R' stands for benzyl or represents the group

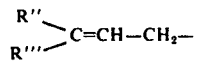

in which R'' and R''' are independently selected from hydrogen and alkyl of from 1 to 4 carbon atoms in an organic solvent, in the presence of a basic catalyst, at from about 140° to about 170°C treating, the obtained product of formula

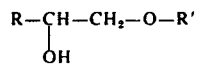    III wherein R and R' have the above meanings, with at least an equimolecular amount of p-toluenesulfonyl halide, at from about −5° to about 20°C in the presence of a tertiary organic nitrogen containing base and reacting in a closed system the resulting compound of formula

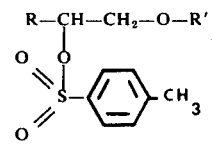    IV wherein R and R' are as above defined, with an excess of gaseous ammonia, in the presence of an inert organic solvent, at from about 95° to about 120°C and recovering the resulting compound of Formula I as acid addition salt.

2. The process as defined in claim 1 and including the steps of treating the acid addition salt of the compound of Formula I with at least an equimolar amount of a base and recovering the corresponding compound of Formula I as a free base.

3. The process as defined in claim 1 wherein from about 5 to about 7 molar equivalents of the alcohol are employed for each molar equivalent of the compound of Formula I.

4. The process as defined in claim 1 wherein from about a 40 to about 60 molar excess of ammonia is employed.

5. The process as defined in claim 4 wherein the reaction period with the ammonia is from about 4 to about 8 hours.

6. A process for preparing the α-aminobutanol of formula

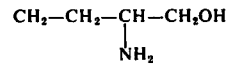

which comprises reacting 1,2-epoxybutane of formula

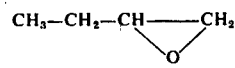

with from about 5 to about 7 molar amounts of benzyl alcohol, in the presence of metallic sodium, for about 2 hours, at about 160°C, treating the obtained product of formula

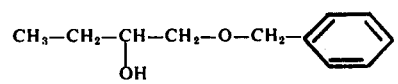

with at least one equimolecular amount of p-toluenesulfonyl chloride at a temperature of about 18°C, for from about 16 to about 20 hours in the presence of pyridine, and reacting in a closed system the resulting compound of formula

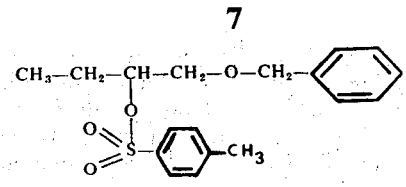
with an excess of gaseous ammonia in an organic solvent, as for instance, ethanol, at a temperature of from about 100° to about 110°C recovering the resulting α-aminobutanol as the hydrochloride, and treating the obtained hydrochloride with one molar equivalent of sodium hydroxide.
* * * * *